US012629486B2

(12) United States Patent
    Blacklock

(10) Patent No.: US 12,629,486 B2
(45) Date of Patent: May 19, 2026

(54) DEVICES AND METHODS TO CREATE A PROTECTIVE GAS CUSHION

(71) Applicant: Christopher Stephen Blacklock, Sidlesham (GB)

(72) Inventor: Christopher Stephen Blacklock, Sidlesham (GB)

( * ) Notice: Subject to any disclaimer, the term of this patent is extended or adjusted under 35 U.S.C. 154(b) by 838 days.

(21) Appl. No.: 17/056,883

(22) PCT Filed: May 20, 2019

(86) PCT No.: PCT/IB2019/054132
    § 371 (c)(1),
    (2) Date: Nov. 19, 2020

(87) PCT Pub. No.: WO2019/224686
    PCT Pub. Date: Nov. 28, 2019

(65) Prior Publication Data
    US 2021/0187213 A1     Jun. 24, 2021

Related U.S. Application Data

(60) Provisional application No. 62/674,266, filed on May 21, 2018.

(51) Int. Cl.
    *A61M 13/00*          (2006.01)
(52) U.S. Cl.
    CPC ... *A61M 13/003* (2013.01); *A61M 2202/0225* (2013.01); *A61M 2205/02* (2013.01); *A61M 2205/7527* (2013.01); *A61M 2206/11* (2013.01)
(58) Field of Classification Search
    CPC .............................. A61G 13/108; A61B 90/40; A61B 2090/401; A61M 2206/11; A61M 13/003;

(Continued)

(56) References Cited

U.S. PATENT DOCUMENTS 3,259,677 A * 7/1966 Zwick .................. B01D 27/005
                                                      249/141
6,994,685 B2   2/2006 Van Der Linden
                (Continued)

FOREIGN PATENT DOCUMENTS

GB         2462429 A      2/2010
WO    WO-02083228 A2 * 10/2002  ............ A61M 5/158

OTHER PUBLICATIONS

Promepla, PE Microporous, XM-1264, Jun. 27, 2017 (Year: 2017).*
                (Continued)

*Primary Examiner* — Courtney Fredrickson
*Assistant Examiner* — Anna E Vargas
(74) *Attorney, Agent, or Firm* — Heslin Rothenberg Farley & Mesiti, P.C.

(57) ABSTRACT

Devices and methods for creating a protective gas cushion in an outwardly open volume which are useful in surgery are provided. More particularly, the invention relates to a device having a flexible hose portion having an intake end and a discharge end and a distal tip portion connected to the discharge end of the flexible hose portion. The distal tip portion comprises a rigid, porous polymer body having a pore size of 7 to 45 μm. The distal tip portion is adapted to be positioned in the volume and the device is arranged to supply the gas to the volume through the rigid, porous polymer body, the rigid, porous polymer body being arranged to supply the volume with the gas in a substantially laminar, continuous flow to enable the formation of the protective gas cushion intended to fill the volume and prevent air from the environment from reaching the volume.

31 Claims, 5 Drawing Sheets

(58) Field of Classification Search
CPC .. A61M 2202/0225; A61M 2025/0057; A61M
25/0067; A61M 25/0068; A61M 25/0069;
A61M 25/007; A61M 25/0082
USPC .......................................................... 604/26
See application file for complete search history.

(56)                     References Cited

U.S. PATENT DOCUMENTS

| | | | |
|---|---|---|---|
| 2005/0119607 A1 | 6/2005 | Van Der Linden et al. | |
| 2014/0188089 A1* | 7/2014 | Midgette | A61M 39/16 |
| | | | 521/143 |

OTHER PUBLICATIONS

International Search Report and Written Opinion of the International Searching Authority for International Application No. PCT/IB2019/054132 mailed on Sep. 20, 2019.

* cited by examiner

DEVICES AND METHODS TO CREATE A PROTECTIVE GAS CUSHION

CROSS REFERENCE TO RELATED APPLICATIONS

This application is a national stage filing under section 371 of International Application No. PCT/IB2019/054132, filed on May 20, 2019, published on Nov. 28, 2019 as WO2019/224686A1 and which claims priority to U.S. Provisional Application No. 62/674,266, filed on May 21, 2018, the entire disclosure of these applications being hereby incorporated herein by reference.

FIELD OF THE INVENTION

The present invention relates to gas insufflators, also known as gas diffusers. In particular, this invention relates to a gas insufflator that is used to create a protective gas cushion in a volume. The invention also relates to methods for creating a protective gas cushion in a volume.

BACKGROUND OF THE INVENTION

During operations which are performed in an open manner, i.e. when an inner portion of the body is uncovered for the performance of the surgical operation, it may be important to prevent air from the environment from reaching the open portion of the body. A gas insufflator (or gas diffuser) can be used to modify the local atmosphere around the operation. In cardiac surgery, $CO_2$ is used to modify the local atmosphere in the chest cavity so that it is as near to 100 percent $CO_2$ as possible. This modification of the local atmosphere has been shown to reduce the number of air emboli and therefore there is a reduction in the potential for a patient to suffer a stroke or organ damage from emboli.

Gas insufflators can be used to create a local $CO_2$ atmosphere when other surgical procedures are being carried out. This will not only reduce the potential of air emboli to form but also has the potential to reduce infections.

When $CO_2$ is being used, the open end of the tube of the gas insufflator is connected to a regulated $CO_2$ source. The diffusing end of the gas insufflator is then placed in the area where the local $CO_2$ atmosphere is required. The $CO_2$ is then turned on and gas flows down the tube and can be diffused to create a local $CO_2$ atmosphere with varying degrees of turbulence, based on the design of the gas insufflator. Minimizing turbulence (i.e., maintaining substantially laminar flow) is desirable to avoid formation of turbulence which would mix of air from the environment with the local $CO_2$ atmosphere.

Gas insufflators are known, but improved gas insufflators that provide a more stable local atmosphere with less turbulence are needed.

SUMMARY OF THE INVENTION

This invention provides a device arranged to create a protective gas cushion in an outwardly open volume, the device being connectable to a gas source, the device comprising: (i) a flexible hose portion having an intake end and a discharge end and (ii) a distal tip portion connected to the discharge end of the flexible hose portion, and the distal tip portion comprising a rigid, porous polymer body having a pore size of 7 to 45 µm. The distal tip portion is adapted to be positioned in the volume and the device is arranged to supply the gas to the volume through the rigid, porous polymer body, the rigid, porous polymer body being arranged to supply the volume with the gas in a substantially laminar, continuous flow in order to enable the formation of the protective gas cushion intended to fill the volume and thereby prevent air from the environment from reaching the volume. The invention also provides a system comprising a gas source and such a device. The intake end of the flexible hose portion being connected to the gas source.

The invention provides a method for creating a protective gas cushion in an outwardly open volume comprising providing such a device; attaching the intake end of the flexible hose portion to a gas source; positioning the distal tip portion in the volume; and supplying the gas to the volume through the device in such a way that a substantially laminar, continuous flow of the gas is formed. The positioning of the distal tip portion in the volume and the supplying of the gas to the volume are performed so that the controlled gas flow forms the gas cushion which substantially fills the volume and thereby prevents air from the environment from reaching the volume.

It is to be understood that both the foregoing general description and the following detailed description are exemplary and explanatory and are intended to provide further explanation of the invention as claimed.

BRIEF DESCRIPTION OF THE DRAWINGS

Preferred forms of the present invention will now be described by way of examples with reference to the accompanying drawings.

DETAILED DESCRIPTION OF THE PREFERRED EMBODIMENTS

Figure 1:
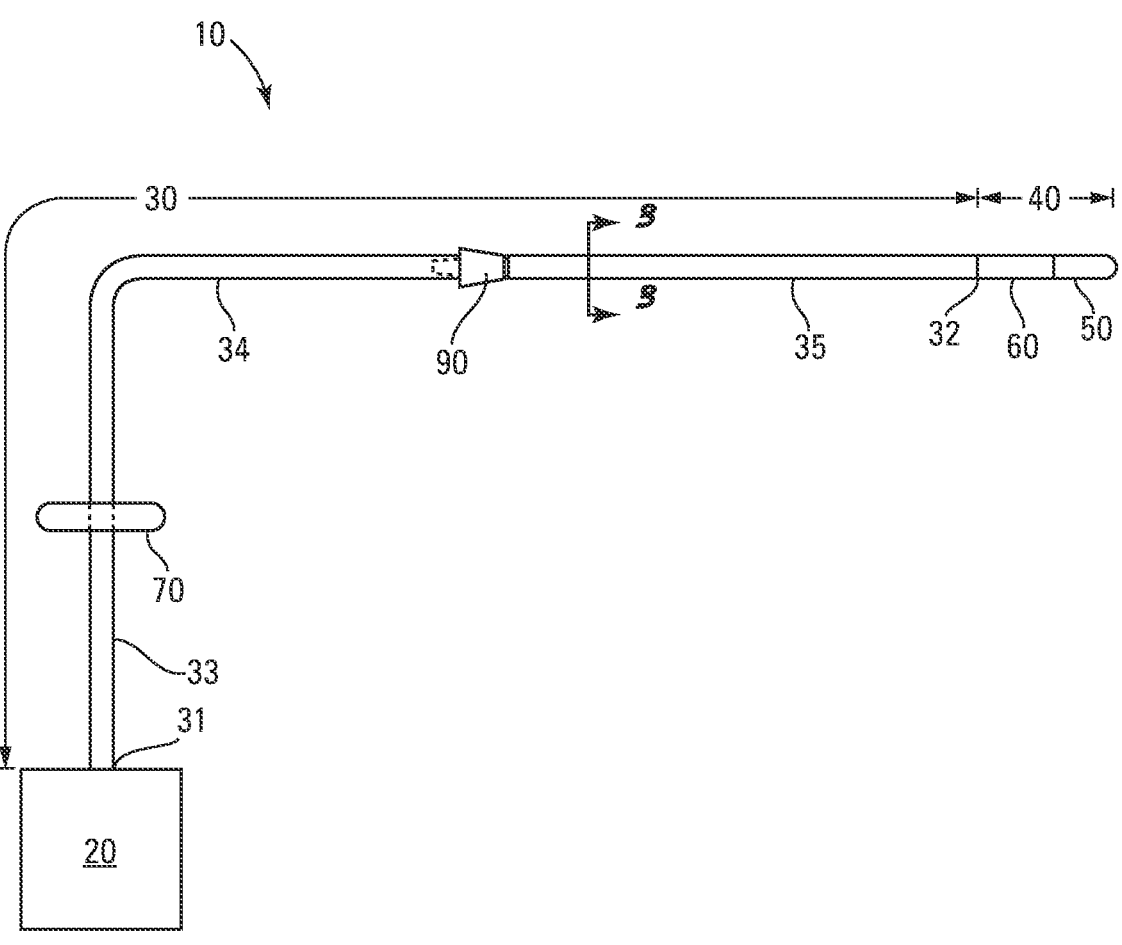
FIG. 1 shows a device of the invention attached to a gas source.

In one embodiment the invention is a device arranged to create a protective gas cushion in an outwardly open volume, the device being connectable to a gas source, the device comprising: (i) a flexible hose portion having an intake end and a discharge end and (ii) a distal tip portion connected to the discharge end of the flexible hose portion, and the distal tip portion comprising a rigid, porous polymer body having a pore size of 7 to 45 µm. The distal tip portion is adapted to be positioned in the volume and the device is arranged to supply the gas to the volume through the rigid, porous polymer body, the rigid, porous polymer body being arranged to supply the volume with the gas in a substantially laminar, continuous flow in order to enable the formation of the protective gas cushion intended to fill the volume and thereby prevent air from the environment from reaching the volume.

The advantage of letting the gas passing through a rigid, porous polymer body having a pore size of 7 to 45 µm is that the pores which are great in number and positioned very closely to each other function as a multiplicity of supply nozzles, and distribute the gas in thin layers lying close to each other and forming, when the gas leaves the rigid, porous polymer body, a substantially laminar continuous gas flow, which enables the formation of the protective gas cushion. The rigid, porous polymer body also causes the gas to exit through pores over the majority of the body thereby preventing a singular jetting action. The rigid, porous polymer body ensures that the gas within the tip and the delivery tube is at a higher velocity than the gas external to the tip, whereby a slow, substantially laminar, continuous gas flow is obtained. The protective gas cushion, which hereby is formed, prevents the surrounding air from reaching the volume filled by the gas cushion and thus also bacteria and other particles which may be present in the surrounding air. When $CO_2$ is the gas, air emboli are reduced. In addition, because the protective gas cushion is formed from a substantially laminar continuous flow of gas, turbulence is minimized and the protective gas cushion maintains separation from the surrounding air.

In an embodiment of the device, the rigid, porous polymer body is hydrophobic. In an embodiment, the rigid, porous polymer body is made of high density polyethylene. In another embodiment, the rigid, porous polymer body comprises a hollow interior portion. In an embodiment, the distal tip portion comprises a rigid, non-porous polymer body proximal of the rigid, porous polymer body. In one embodiment, the flexible hose portion comprises a filter to remove impurities from the gas. In an embodiment, the flexible hose portion has a length and comprises a malleable wire for at least a portion of its length. In one embodiment, the rigid, porous polymer body is arranged to supply the gas in several directions from the rigid, porous polymer body. In an embodiment, the rigid, porous polymer body has a pore size of 25 to 45 μm.

The invention also provides a system comprising a gas source and such a device. The intake end of the flexible hose portion of the device being connected to the gas source. In an embodiment, the gas comprises a majority of carbon dioxide.

The invention provides a method for creating a protective gas cushion in an outwardly open volume comprising providing such a device; attaching the intake end of the flexible hose portion to a gas source; positioning the distal tip portion in the volume; and supplying the gas to the volume through the device in such a way that a substantially laminar, continuous flow of the gas is formed. The positioning of the distal tip portion in the volume and the supplying of the gas to the volume are performed so that the controlled gas flow forms the gas cushion which substantially fills the volume and thereby prevents air from the environment from reaching the volume. In an embodiment, the outwardly open volume adjoins a portion of the body of a living organism, the portion of the body being a portion that is normally not exposed to the atmosphere. In one embodiment, the living organism is a human. In an embodiment, the gas comprises a majority of carbon dioxide.

The invention provides a device for creating a protective gas cushion in an open volume that adjoins a temporarily open, inner portion of a human being in order to prevent air from the environment from reaching the volume. Such an open portion is formed during operations performed openly, i.e., when an inner portion of the body is uncovered for performing a surgical operation. For instance, during heart operations a substantial part of the interior of the thorax is uncovered so that this interior portion in normal cases has direct contact with the surrounding air.

FIG. 1 shows a gas insufflator device 10 of the invention connected to a gas source 20. The gas insufflator device has a flexible hose portion 30 and a distal tip portion 40. Distal tip portion 40 includes a rigid, porous polymer body 50 at its end. The rigid, porous polymer body 50 has a pore size of 7 to 45 μm, is made of high density polyethylene, and is hydrophobic.

The high density polyethylene that rigid, porous polymer body 50 is made of was obtained from Porex Corporation, Fairburn, Georgia, USA and is designated XM-1264. A single pore size measurement on the XM-1264 used in rigid, porous polymer body 50 yielded the following value: Pore size 29.51 μm. Pore size was measured using the Mercury Intrusion Method. In a vacuum, a mercury drop will not enter a pore due to its very high surface tension, but will if pressure is applied. It is known that, for a given pore size, a certain pressure is required to force the mercury into the pore. For each incremental increase in pressure, the change in intrusion volume is equal to the volume of the pores whose diameters fall within an interval that corresponds to the particular pressure interval. The amount of displaced mercury can therefore be used to calculate the pore size using a graphical representation. The pore size will be the average size of the pore distribution obtained (i.e. the peak value).

Figure 5:
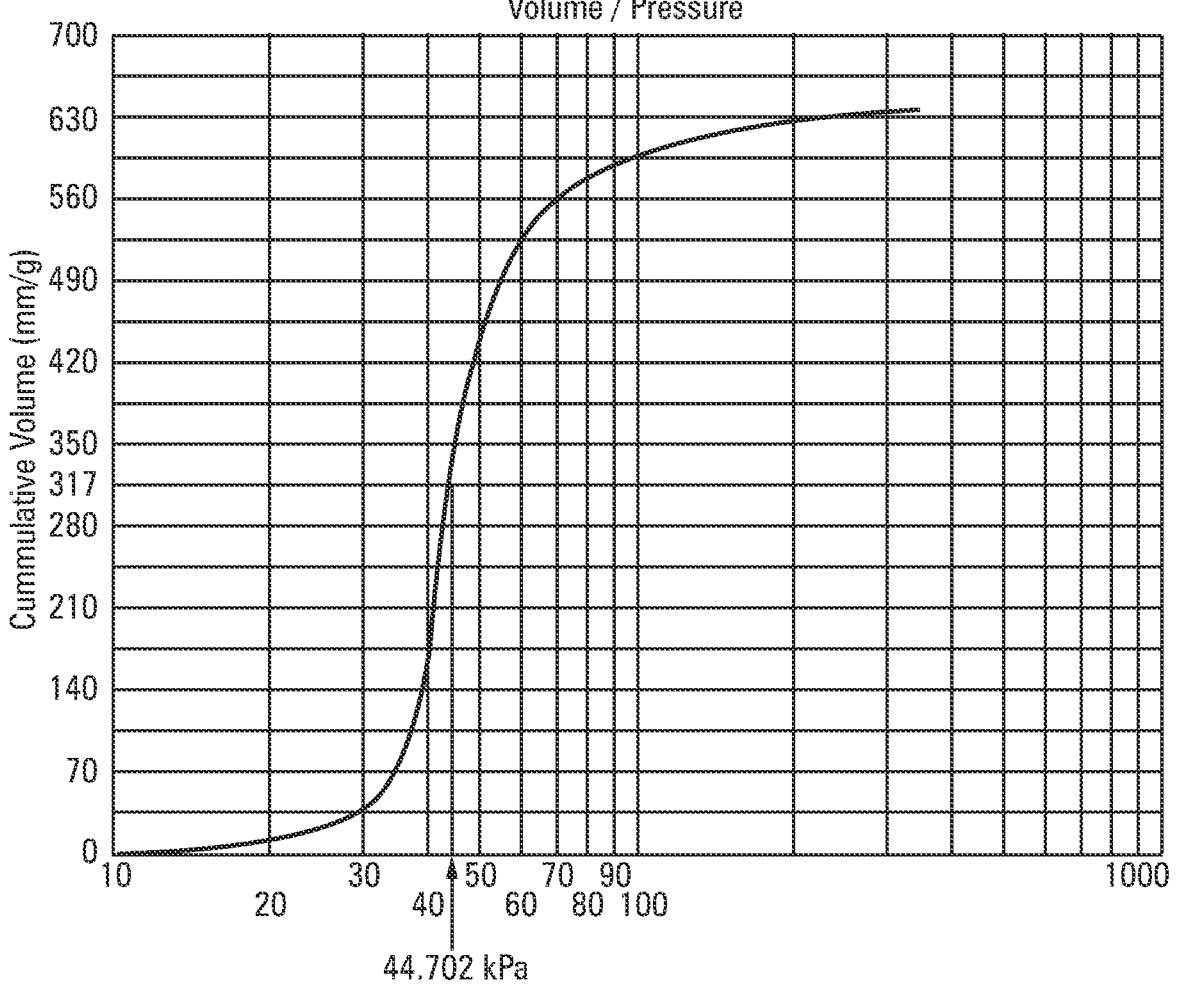
FIG. 5 shows a graph of cumulative volume v. pressure, which is used in the calculation of pore size.

The Washburn Equation was used to convert pressure to pore diameter:

$$D = -4y(\cos \theta)/P$$

where D=Diameter of pore being intruded
y=Surface tension of mercury
P=Intrusion pressure
θ=contact angle between mercury & material For example, to arrive at a pore size of 29.51 μm for combined bodies 50 and 60, y is 480 N/m, θ is 133.4°, and P is 44.702 kPa. The intrusion pressure is the pressure at which 50% of the volume of mercury intrudes into the pores. From the graph for XM-1264 material shown in FIG. 5, the total volume is 634 $mm^3$/g, and so 50% is 317 $mm^3$/g. This pressure cuts the curve at 44.702 kPa.

So, we have D=−4×480×(cos 133.4°)/44.702=29.51 μm. This is the "50% value". It means that 50% of the pores lie above this diameter and 50% lie below it. Pore size in this application, including the claims, means this 50% value, with 50% of the pores being above this diameter and 50% being below it.

High density polyethylene is a thermoplastic polymer having at least partially crystalline properties and a low degree of branching. The pore size of the rigid, porous polymer body 50 means that the gas, preferably $CO_2$, is diffused over its full surface. The small pore size means that even at flows as low at 2.5 liters per minute (LPM) it will still act as a very efficient gas diffuser. The smaller pore size means in effect that the gas has to make more effort to exit the rigid, porous polymer body 50 and flows through more pores. So rather than having individual jets of gas exiting various points on the diffusing material, an instantaneous atmosphere is formed around the rigid, porous polymer body 50 once the gas source is turned on. The device 10 creates an instantaneous local atmosphere at the majority of points perpendicular to the surface of the rigid, porous polymer body 50 to a distance of 5 mm at a flow of 2 LPM or above. The rigid, porous polymer body 50 will only absorb blood and cause a subsequent restriction of gas flow if a negative pressure has been applied to the open end of the tube, which would draw blood into the tube. With larger pore sizes, jets of gas are produced and cause more turbulence, which increases the chance that the surrounding air could be drawn into the surgical field. Pore sizes larger than 45 micron also lead to the possibility of air being entrained into the filter material from the atmosphere when the delivery gas is being used. This air can potentially merge with the delivery gas. This occurs as a negative pressure area is created in the pores where gas is not exiting as the delivery gas passes out through the pores of least resistance.

Figure 2:
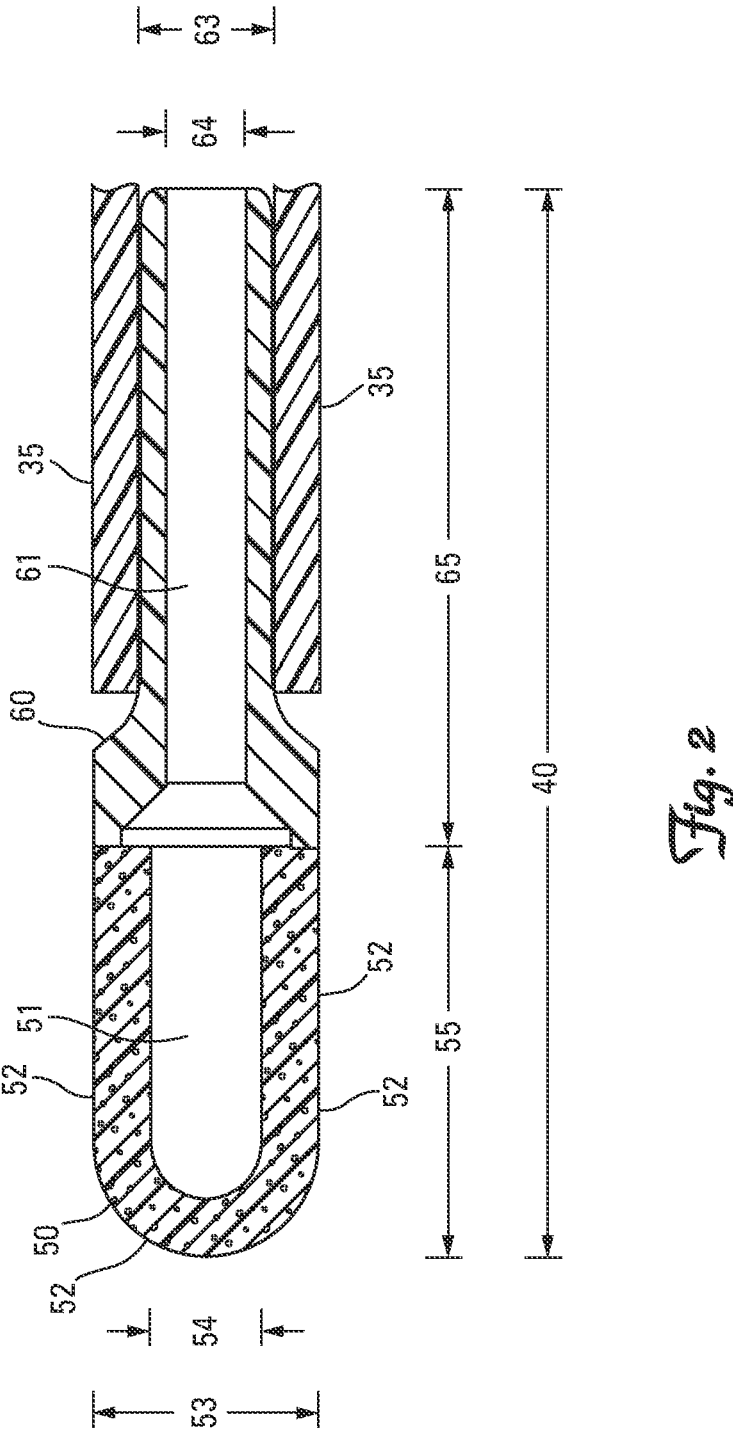
FIG. 2 shows a cross-sectional view of the distal tip portion of the device.

The distal tip portion includes a rigid, non-porous polymer body 60 proximal of the rigid, porous polymer body 50. As shown in FIG. 2, a portion of rigid, non-porous polymer body 60 has a smaller exterior diameter than rigid, porous polymer body 50. Flexible hose 35 extends over the smaller exterior diameter portion of rigid, non-porous polymer body 60. The rigid, porous polymer body 50 has a hollow interior portion 51 and rigid, non-porous polymer body 60 has a hollow interior portion 61. The rigid, non-porous polymer body 60 is made of high density polyethylene.

The hollow interior portion 51 of rigid, porous polymer body 50 has a transverse diameter 54 of 3.6 mm and the exterior diameter 53 is 7.0 mm. The rigid, porous polymer body 50 has a length 55 of 12.5 mm. For the majority of its length, the hollow interior portion 61 of rigid, non-porous polymer body 60 has a transverse diameter 64 of 2.55 mm and the exterior diameter 63 is 3.95 mm. The rigid, non-porous polymer body 60 has a length 65 of 19.5 mm.

Gas flows from gas source 20 through flexible hose 33, filter 70, flexible hose 34, connector 90, the portion of flexible hose 35 that does not contain the smaller exterior diameter portion of rigid, non-porous polymer body 60, hollow interior portion 61 of rigid, non-porous polymer body 60, hollow interior portion 51 of rigid, porous polymer body 50 and through the multiplicity of pores 52 of rigid, porous polymer body 50 (pores 52 are indicated in FIG. 2 but are too small to actually be seen).

Flexible hose portion 30 includes flexible hose 33, filter 70, flexible hose 34, connector 90, and that portion of flexible hose 35 that does not contain the smaller exterior diameter portion of rigid, non-porous polymer body 60. Distal tip portion 40 includes rigid, non-porous polymer body 60, rigid, porous polymer body, and the portion of flexible hose 35 that does contain the smaller exterior diameter portion of rigid, non-porous polymer body 60.

Figure 3:
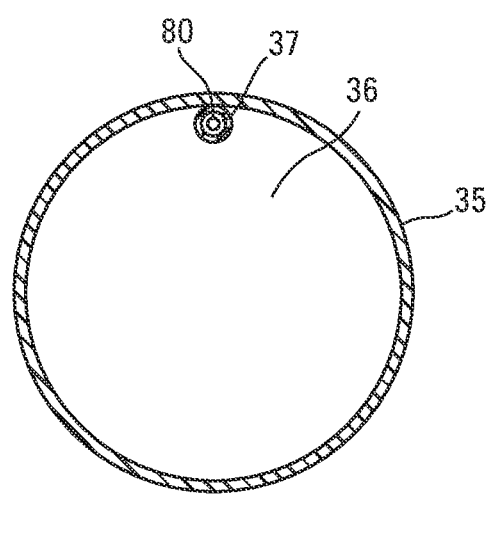
FIG. 3 shows a cross-sectional view of a portion of the flexible hose portion of the device.

Flexible hose 33 connects gas source 20 to filter 70. Flexible hose 33 is made of ¼ inch (internal diameter) PVC tubing. The filter 70 has a housing made of polypropylene and glass fibers as a filter material. Filter 70 is used to remove impurities from the gas. Filter 70 preferably has a pore size between 0.1 to 0.4 μm. Flexible hose 34 connects gas source filter 70 to connector 90. Flexible hose 34 is made of ¼ inch PVC tubing. Connector 90 is used to reduce the diameter of the gas flow path. Flexible hose 35 connects connector 90 to rigid, non-porous polymer body 60. Although the portion of polymer body 60 in contact with flexible hose 35 is smooth as shown in FIG. 2, the portion of polymer body 60 in contact with flexible hose 35 can include one or more barbs, preferably formed into the polymer body 60, to secure flexible hose 35 to polymer body 60. Flexible hose 35 has a smaller diameter than flexible hose 34 and is made of PVC. The interior diameter of flexible hose 35 is 3.9 mm. Flexible hose 35 has two lumens, a first lumen 36 allowing the passage of gas and second lumen 37, which contains malleable wire 80. See FIG. 3. Malleable wire 80 is made of stainless steel and has a diameter of 0.97 mm. Malleable wire 80 allows flexible hose 35 to be shapeable to be best positioned in use. In an alternative embodiment, the device 10 does not include the malleable wire 80. As shown in FIG. 2, rigid, non-porous polymer body 60 is attached to rigid, porous polymer body 50. As shown in FIGS. 1 and 2 the end of the rigid, porous polymer body 50 is hemispherical. The attachment of the various components can be made by methods known in the art, such as adhesives, friction fits, etc.

Figure 4:
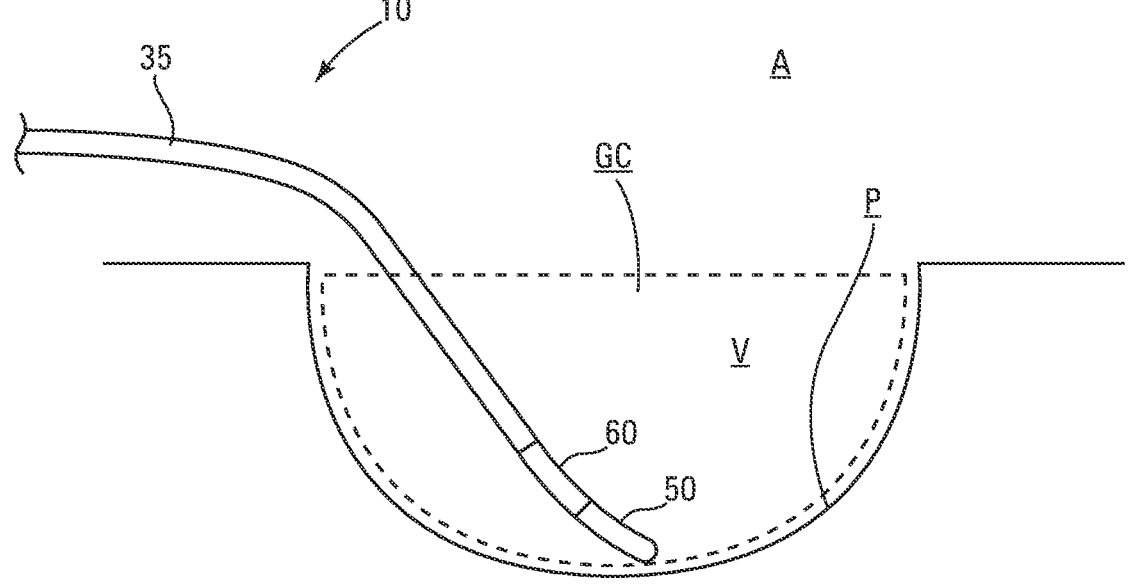
FIG. 4 shows a diagram of the device of the invention in use.

FIG. 4 shows device 10 in use. Rigid, porous polymer body 50 has placed in outwardly open volume V and adjacent to a portion P of a human body that is normally not exposed to the atmosphere, as in a surgery. Gas source 20 has been turned on and protective gas cushion GC has been formed, which fills the volume V and prevents air A from the environment from reaching the volume. As $CO_2$, the preferred gas, is heavier than air, the $CO_2$ will accumulate in the volume V as long as the gas flow into the volume V is not turbulent.

In order to prevent air embolism, i.e., a blocking of the capillaries and small vessels, which may be caused by an air bubble, the protective gas cushion in a volume adjoining a temporarily, outwardly open portion of a human being, ought to include a gas, the majority of the gas is carbon dioxide. In the applications where a protective gas cushion is to be created in a volume adjoining an outwardly open inner portion of the body of a human being or an animal, it is advantageous that the gas includes carbon dioxide due to the fact that carbon dioxide has a high solubility in the tissue of the body relative to oxygen and nitrogen. In addition, carbon dioxide has at least a bacteriostatic function, which reduces the growth of bacteria and/or other microorganisms, which possibly may be present in the open portion. Furthermore, carbon dioxide is heavier than air so that a protective gas cushion in a volume adjoining an outwardly open, inner portion of a human being may be created in an easy manner. It is to be noted that the gas may be supplied to the volume in a continuous flow, wherein it is possible to ensure that the surrounding air is prevented from reaching the volume even if a part of the supplied gas leaves the area. Another possibility is, at least initially, to supply gas continuously in order to create the protective gas cushion, and then supply gas periodically to maintain the gas cushion. The device may be combined by a gas sensing member, which is arranged to sense the concentration of the supplied gas or air in the volume. By means of such a sensing, the gas supply to the actual volume may be controlled in such a way that if an increased air concentration is noted, the gas supply is also increased, or if the air concentration in the actual volume exceeds a predetermined level the gas supply is increased. It should also be noted that the gas may include oxygen, for instance in the cases when said tissue of said open body portion is strongly oxygen dependent. Oxygen, as well as carbon dioxide, is heavier than air so that the protecting atmosphere in the volume may be created in an easy manner since the heavier gas will pass downwardly in the open body portion and force away the non-sterile air present in the lower part of this open portion.

In an embodiment of the invention, the gas includes air. In certain applications a protecting atmosphere including sterile air may be satisfactory. The main thing is that air from the environment, i.e., non-sterile air, is prevented from reaching the volume.

Although particular embodiments have been disclosed herein in detail, this has been done for purposes of illustration only, and is not intended to be limiting with respect to the scope of the following appended claims. In particular, it is contemplated by the inventors that various substitutions, alterations, and modifications may be made to the invention without departing from the spirit and scope of the invention as defined by the claims.

The invention claimed is:

1. A device arranged to create a protective gas cushion in an outwardly open volume, the device being connectable to a gas source, the device comprising: (i) a flexible hose portion having an intake end and a discharge end and (ii) a distal tip portion connected to the discharge end of the flexible hose portion, the distal tip portion comprising a rigid, non-porous polymer body connected to a rigid, porous polymer body, the rigid, porous polymer body having a pore size of 7 to 45 μm, wherein the distal tip portion is adapted to be positioned in the volume and wherein the device is arranged to supply the gas to the volume through a first hollow interior portion of the rigid, porous polymer body, the rigid, porous polymer body being arranged to supply the volume with the gas in a substantially laminar, continuous flow, such that the protective gas cushion intended to fill the volume and thereby prevent air from the environment from reaching the volume is formed upon the gas passing through the rigid, porous polymer body; and wherein the rigid, non-porous polymer body has a second hollow interior portion which is longer than the first hollow interior portion.

2. The device of claim 1, wherein the rigid, porous polymer body is hydrophobic.

3. The device of claim 1, wherein the rigid, porous polymer body is made of high density polyethylene.

4. The device of claim 1, wherein the flexible hose portion comprises a filter to remove impurities from the gas.

5. The device of claim 1, wherein the flexible hose portion has a length and comprises a malleable wire for at least portion of its length.

6. The device of claim 1, wherein the rigid, porous polymer body is arranged to supply the gas in several directions from the rigid, porous polymer body.

7. The device of claim 1, wherein the rigid, porous polymer body has a pore size of 25 to 45 μm.

8. The device of claim 1, wherein the first hollow interior portion has a first transverse diameter which is larger than a second transverse diameter of the second hollow interior portion.

9. The device of claim 1, wherein the rigid, non-porous polymer body further comprises:

a first portion connected the rigid, porous polymer body; and a second portion connected to the first portion;

wherein the second hollow interior portion extends through at least part of the first portion and the second portion; and wherein the first portion has a first exterior diameter which is larger than a second exterior diameter of the second portion.

10. The device of claim 9, wherein the rigid, non-porous polymer body further comprises a curved edge connecting an outer surface of the first portion to an outer surface of the second portion, such that the rigid, non-porous polymer body narrows from the first portion to the second portion.

11. The device of claim 9, wherein the first exterior diameter of the rigid, non-porous polymer body is equal to a third exterior diameter of the rigid, porous polymer body, and wherein the second exterior diameter is smaller than the third exterior diameter.

12. The device of claim 1, wherein a first exterior diameter of the rigid, non-porous polymer body is smaller than a second exterior diameter of the rigid, porous polymer body.

13. The device of claim 1, wherein a first total length of the rigid, porous polymer body is shorter than a second total length of the rigid, non-porous polymer body.

14. A system comprising a gas source and a device, the device being arranged to create a protective gas cushion in an outwardly open volume, the device being connectable to the gas source, the device comprising: (i) a flexible hose portion having an intake end and a discharge end and (ii) a distal tip portion connected to the discharge end of the flexible hose portion, the distal tip portion comprising a rigid, non-porous polymer connected to a rigid, porous polymer body, the rigid, porous polymer body having a pore size of 7 to 45 μm, wherein the distal tip portion is adapted to be positioned in the volume and wherein the device is arranged to supply the gas to the volume through a first hollow interior portion of the rigid, porous polymer body, the rigid, porous polymer body being arranged to supply the volume with the gas in a substantially laminar, continuous flow, such that of the protective gas cushion intended to substantially fill the volume and thereby prevent air from the environment from reaching the volume is formed upon the gas passing through the rigid, porous polymer body, and the intake end of the flexible hose portion being connected to the gas source; and wherein the rigid, non-porous polymer body has a second hollow interior portion which is longer than the first hollow interior portion.

15. The system of claim 14, wherein the rigid, porous polymer body is hydrophobic.

16. The system of claim 14, wherein the rigid, porous polymer body is made of high density polyethylene.

17. The system of claim 14, wherein the flexible hose portion comprises a filter to remove impurities from the gas.

18. The system of claim 14, wherein the flexible hose portion has a length and comprises a malleable wire for at least portion of its length.

19. The system of claim 14, wherein the rigid, porous polymer body is arranged to supply the gas in several directions from the rigid, porous polymer body.

20. The system of claim 14, wherein the rigid, porous polymer body has a pore size of 25 to 45 μm.

21. The system of claim 14, wherein the gas comprises a majority of carbon dioxide.

22. A method for creating a protective gas cushion in an outwardly open volume comprising:

providing a device arranged to create a protective gas cushion in an outwardly open volume, the device comprising: (i) a flexible hose portion having an intake end and a discharge end and (ii) a distal tip portion connected to the discharge end of the flexible hose portion, the distal tip portion comprising a rigid, non-porous polymer body connected to a rigid, porous polymer body, the rigid, porous polymer body having a pore size of 7 to 45 μm, connecting the intake end of the flexible hose portion to a gas source, and positioning the distal tip portion in the volume and supplying the gas to the volume through a first hollow interior portion of the rigid, porous polymer body to supply the volume with the gas in a substantially laminar, continuous flow to form the protective gas cushion to substantially fill the volume and thereby prevent air from the environment from reaching the volume;

wherein the rigid, non-porous polymer body has a second hollow interior portion which is longer than the first hollow interior portion.

23. The method of claim 22, wherein the rigid, porous polymer body is hydrophobic.

24. The method of claim 22, wherein the rigid, porous polymer body is made of high density polyethylene.

25. The method of claim 22, wherein the flexible hose portion comprises a filter to remove impurities from the gas.

26. The method of claim 22, wherein the flexible hose portion has a length and comprises a malleable wire for at least portion of its length.

27. The method of claim 22, wherein the rigid, porous polymer body is arranged to supply the gas in several directions from the rigid, porous polymer body.

28. The method of claim 22, wherein the rigid, porous polymer body has a pore size of 25 to 45 μm.

29. The method of claim 22, wherein the outwardly open volume adjoins a portion of the body of a living organism, the portion of the body being a portion that is normally not exposed to the atmosphere.

30. The method of claim 29, wherein the living organism is a human.

31. The method of claim 22, wherein the gas comprises a majority of carbon dioxide.

* * * * *